United States Patent [19]
Weldon et al.

[11] Patent Number: 5,330,446
[45] Date of Patent: Jul. 19, 1994

[54] WOUND TREATING DEVICE USING AN INFLATABLE MEMBRANE AND METHOD FOR TREATING WOUNDS

[76] Inventors: Thomas D. Weldon; Charles E. Larsen, both of P.O. Box 5149, Aquadilla, P.R. 00605

[21] Appl. No.: 899,507

[22] Filed: Jun. 16, 1992

Related U.S. Application Data

[63] Continuation-in-part of Ser. No. 634,406, Dec. 27, 1990, Pat. No. 5,129,882.

[51] Int. Cl.⁵ .............................................. A61M 5/00
[52] U.S. Cl. ..................................... 604/271; 604/53;
604/96; 606/213; 606/195
[58] Field of Search ............... 606/195, 213; 604/38, 604/46–47, 52, 57, 59–60, 93, 96, 171, 173, 271, 53

[56] References Cited

U.S. PATENT DOCUMENTS

| | | | |
|---|---|---|---|
| 4,271,839 | 6/1981 | Fogarty et al. | 604/52 X |
| 4,471,779 | 9/1984 | Antoshkiw et al. | 606/195 |
| 4,545,367 | 10/1985 | Tucci | 606/195 X |
| 4,638,803 | 1/1987 | Rand | 606/195 X |
| 4,779,611 | 10/1988 | Grooters et al. | 128/4 |
| 4,900,303 | 2/1990 | Lemelson | 604/54 |
| 5,108,421 | 4/1992 | Fowler | 606/213 |

FOREIGN PATENT DOCUMENTS

| | | | |
|---|---|---|---|
| 0210160 | 1/1987 | European Pat. Off. | A61M 5/18 |
| 0367516 | 5/1990 | European Pat. Off. | A61B 17/12 |
| 8911301 | 11/1989 | World Int. Prop. O. | A61M 1/03 |
| 9014796 | 12/1990 | World Int. Prop. O. | A61B 17/12 |

OTHER PUBLICATIONS

European Search Report for corresponding application 91122304.8 filed on Dec. 27, 1991.

*Primary Examiner*—C. Fred Rosenbaum
*Assistant Examiner*—Corrine Maglione
*Attorney, Agent, or Firm*—Cook, Egan, McFarron & Manzo

[57] ABSTRACT

A wound clotting device includes a tubular portion having a proximal end, a distal end and a lumen extending therebetween, an inflatable membrane associated with the distal end of the tubular portion and being moveable between a retracted position and an inflated position to form a balloon-like projection at the distal end when moved to the inflated position for treating a wound. A method for treating a wound by providing a wound-treating device, positioning the device in a location near the wound, moving an inflation membrane of the wound treating device to an inflated position near the wound, and removing the treating device is described. Finally, an alternate wound treating device having an inflatable membrane which is releasably carried at the distal end of the tubular portion and which is expelled to treat the wound is also described.

19 Claims, 10 Drawing Sheets

WOUND TREATING DEVICE USING AN INFLATABLE MEMBRANE AND METHOD FOR TREATING WOUNDS

The instant application is a continuation-in-part of application Ser. No. 634,406 filed Dec. 27, 1990, which issued as U.S. Pat. No. 5,129,882 on Jul. 14, 1992.

BACKGROUND

The present invention relates, in general, to devices and methods for stopping an undesirable flow of fluid between two contiguous tissue samples, such as bleeding from a blood vessel after removal of a medical device, catheter system, or the like. More particularly, the present invention concerns a novel wound treating device which includes means for depositing a treating agent at a wound or aperture between two contiguous tissue areas, such as depositing a clotting agent at the opening in a blood vessel or the like following removal of a medical device or instrument therefrom. The present invention also concerns a novel method for using such a wound treating device.

Many medical procedures, including both therapeutic and diagnostic procedures, often require access between two contiguous tissue areas, such as through the skin and into the vascular system of the patient. As an example, although various means may be used to obtain access into a vein or artery, typically access is obtained by inserting a cannula or catheter (called an introducer catheter or sheath) through the skin and into the selected blood vessel. A medical or diagnostic instrument, such as a guide wire, guiding catheter, balloon angioplasty device, atherectomy device, or the like is then inserted into the vascular system through the introducer catheter.

Depending on the procedure, to permit the insertion of the diagnostic or therapeutic device therethrough, the introducer sheath must be of relatively large diameter. This, of course, results in a relatively large hole or aperture in the vessel wall. After the medical procedure is completed, however, this opening must be closed, and bleeding from the blood vessel stopped.

A common technique to stop such bleeding, as in cardiac balloon angioplasty procedures, is for a nurse or technician to manually apply direct and continuous pressure on the opening in the blood vessel until the blood clots. This may require an hour or more of medical personnel time. Unfortunately, when this procedure is utilized, there is also a significant chance that movement by the patient will reopen the opening and that it will begin bleeding again, resulting in a hematoma or other complications. Because of the risk of bleeding, patients are usually required to remain overnight in the hospital for rest and observation, thus greatly increasing the cost of the overall procedure.

One prior device for stopping bleeding from an aperture in a blood vessel is a type of expandable plug. The plug is pushed through the opening into the blood vessel and into the blood stream. Once in the blood stream, it expands. The expanded plug is then pulled back against the aperture where, because of its expanded size, it plugs the opening. Such a device may work satisfactorily, but requires inserting and leaving a foreign object in the vessel. It is usually medically preferable to avoid inserting and leaving objects in a vessel.

Accordingly, it is a general object of the present invention to provide a wound treating device, as well as a method for using such device, which are particularly useful in treating and assisting in treating wounds such as vascular wounds that result from insertion of a medical device, such as a catheter, and which do not suffer from the drawbacks described above.

SUMMARY OF THE INVENTION

The wound treating device of the present invention comprises generally a tubular portion having a proximal end, a distal end and a lumen extending therebetween. An inflatable means in the form of a flexible inflatable membrane is positioned within the distal end of the tube and is movable between a retracted position within the distal end and an inflated position to form a balloon-like projection at the distal end of the tube. The proximal end of the tubular portion is adapted to receive means, such as a syringe, for moving the inflatable means between the retracted position and the inflated position.

Inflation of the membrane may serve not only to retain the device at the desired location adjacent the wound site, but may also serve to apply a treating agent to the wound. The treating agent may, for example, be contained in a pocket formed by the membrane when it is located in the distal end of the tube, or it may be coated on the surface of the membrane. In either situation, the membrane preferably has any suitable release agent known in the art on the surface to permit ready release of the membrane after treatment.

Further according to the present invention, treating of a wound, such as aiding in the clotting of an aperture in a blood vessel, may be performed utilizing a wound clotting or treating device as described above, with or without an introducer sheath or cannula. When an introducer sheath is utilized, following removal of the diagnostic or therapeutic device, the introducer cannula is retracted from the wound (in this case a blood vessel) until the distal end of the introducer is in the proximity of but spaced from the exterior of the blood vessel. While the introducer is at that position, the distal end of the wound treating device of the present invention is inserted into the introducer and advanced until it extends beyond the distal end of the introducer and is adjacent to the wound, i.e., the opening or aperture in the blood vessel. The inflatable means on the distal end of the device is then inflated to hold the distal end adjacent to the wound and to apply any treating or clotting agent associated with the membrane. After sufficient time has elapsed, the membrane is then deflated, and the device and the introducer sheath are withdrawn from the patient, leaving no substantial foreign matter within the vessel of the patient as a result of this method. The same procedure also may be used without an introducer sheath.

In accordance with another embodiment of the wound treating device of the present invention the inflatable membrane is detachable. In this embodiment, the device includes a tube portion having a proximal end, a distal end and a lumen extending therebetween. The membrane is removably carried at the distal end of the tube portion and includes a piercable resealable portion disposed within the distal end of the tube. Means, such as a partition or piercable plug is fixedly located in the tube proximal of the membrane to define a pressurization chamber between the membrane and the plug. A fitment is located at the proximal end of the tube and is axially movable relative to the tube. Means defining a fluid flow path, such as a pre-attached cannula or needle, extends from the fitment, through the lumen of the tube, to a position near the distal end of the tube.

In operation, the tube is axially adjusted relative to the fitment so that the cannula extends through the pressurization chamber and through the piercable portion of the membrane. Fluid under pressure is forced through the cannula, as by a syringe, and inflates the membrane at the desired location adjacent to the wound site. The tube is then axially adjusted relative to the fitment so that the end of the cannula is withdrawn to a position within the pressurization chamber between the fixed plug and the membrane. Pressurization of this chamber forces the inflated membrane from the end of the tube, allowing removal of the tube, while the inflated membrane remains in place at the wound site.

These and additional features and advantages of the present invention will become more apparent from the following detailed description of the invention, as exemplified in the accompanying drawings.

DETAILED DESCRIPTION OF THE INVENTION

Figures 1, 2:
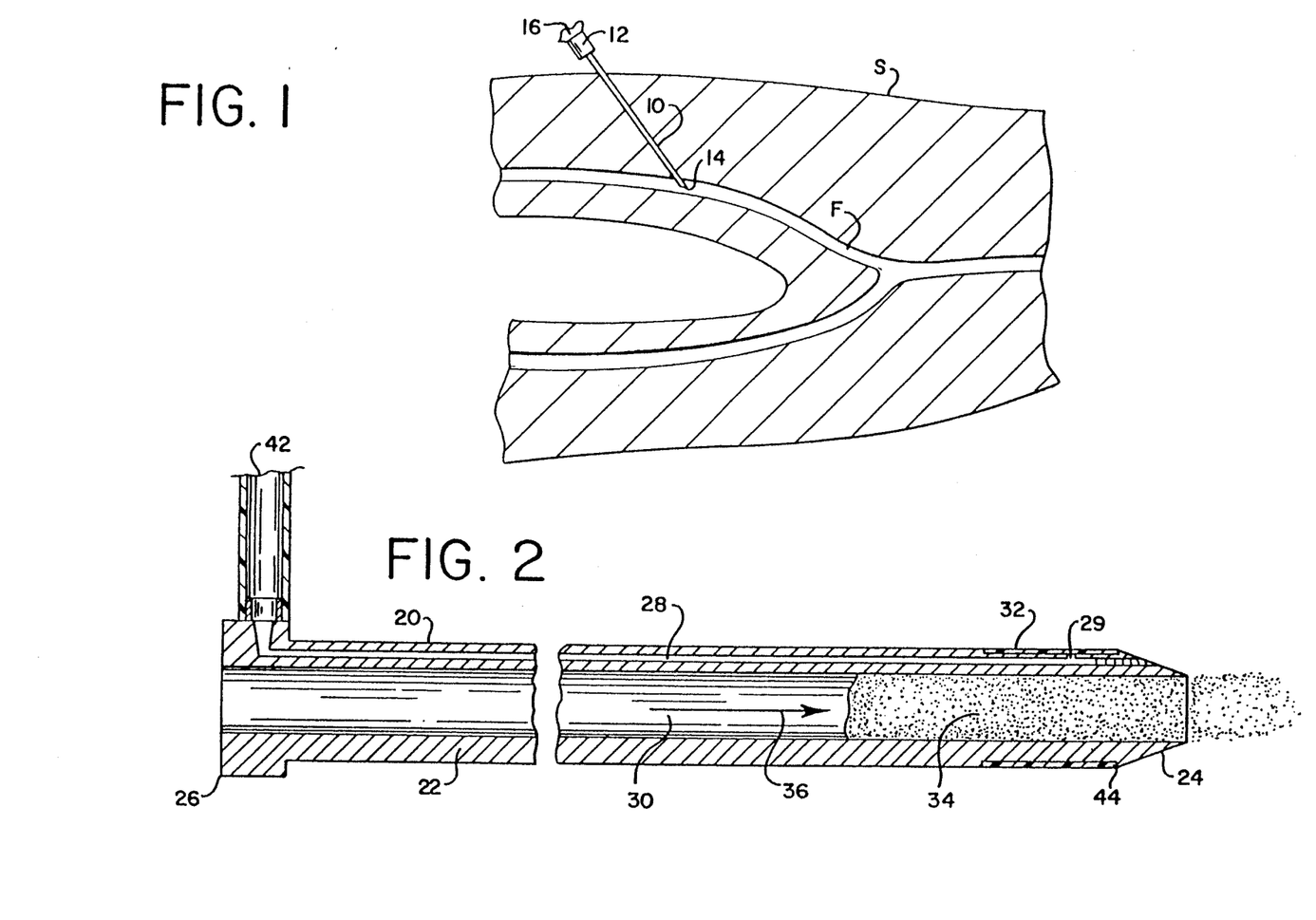
FIG. 1 is a fragmentary diagrammatic view of a sheath introducer extending through the skin into a femoral artery of a patient.
FIG. 2 is an enlarged cross-sectional view of the proximal and distal end portions of a wound treating or clotting device of the present invention with a means for dispensing a clotting agent shown diagrammatically.

FIG. 1 is a partial diagrammatic representation of a sheath introducer 10 which has been advanced through the skin surface S into a femoral artery F of a living patient. The sheath introducer 10 is shown in the femoral artery F for purposes of illustration only and not for purposes of limitation. It is understood that a sheath introducer can also be used in accessing other arteries, veins, or blood vessels, or in communicating between other contiguous tissue areas of a patient's body.

As shown in the exemplary procedure of FIG. 1, the sheath introducer 10 is initially advanced through a patient's skin and into the artery F. The sheath introducer 10 has a resealable valve 12 located at its proximal end 16, as is well known in the medical field. In the typical procedure, some type of medical device, for example, a guiding catheter, an angioplasty device, or the like, is inserted into the sheath introducer through the valve and advanced into the artery and then to the location of the procedure. After the medical device has been used, it is withdrawn from the artery and the sheath introducer. The sheath introducer 10 must then be removed from the artery F. This, of course, leaves an aperture or opening in the artery F (See FIGS. 6 and 7). To assist in stopping bleeding from the opening in the artery, the wound treating device of the present invention may be utilized.

Figure 3:
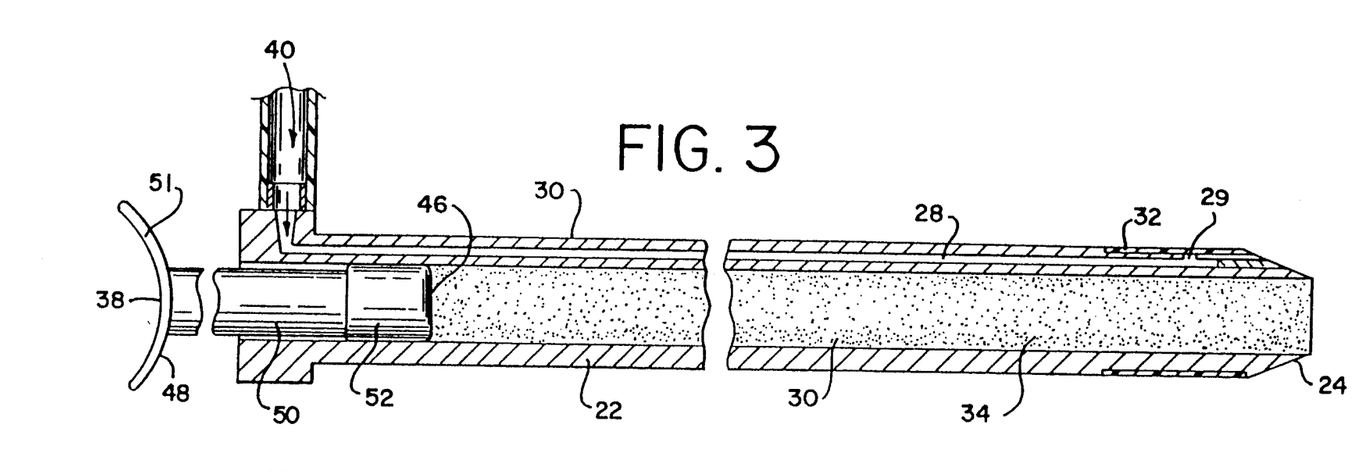
FIG. 3 is a cross-sectional view showing the proximal and distal ends of one embodiment of the wound treating or clotting device of the present invention utilizing a plunger for dispensing the clotting agent and containing a quantity of clotting agent.
Figure 4:
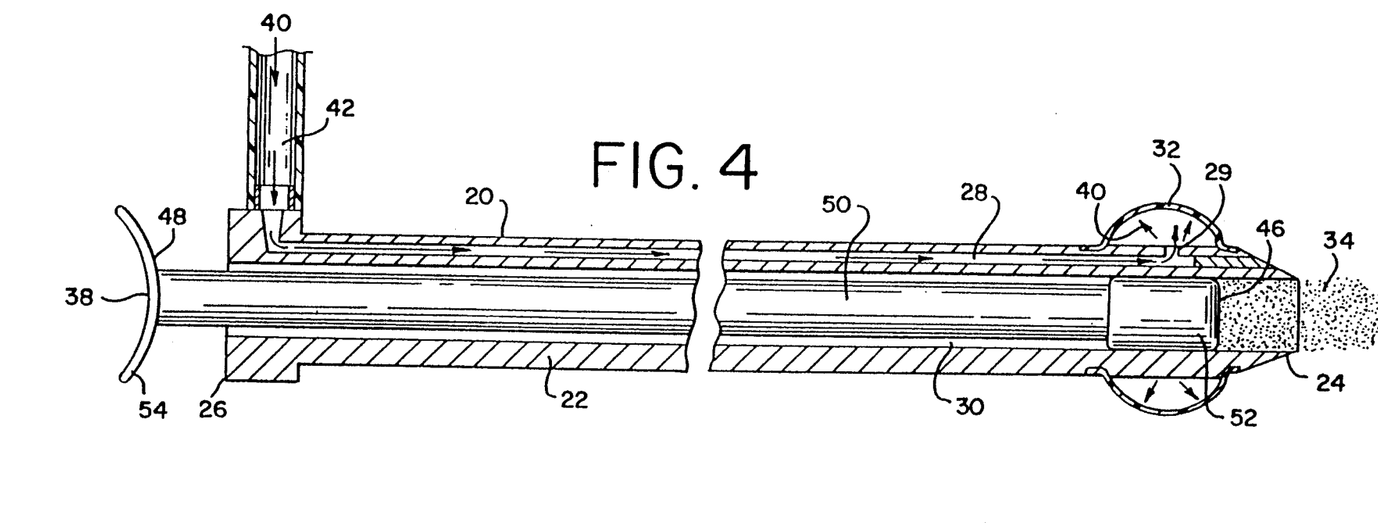
FIG. 4 is a cross-sectional view of the wound treating or clotting device of FIG. 3 showing the inflatable retention means inflated and a plunger ejecting the clotting agent from the device's distal end.

FIGS. 2, 3, and 4 show, in an enlarged view, various embodiments of the wound treating or clotting device of the present invention. With reference to these figures, the wound treating device 20 of the present invention comprises a tube, generally at 22, with a distal end portion generally at 24 and a proximal end portion generally at 26. A relatively large second lumen 30 and a smaller inflation lumen 28 extend between the proximal end 26 to the distal end 24 of the tube 22. The second lumen 30 is open at the distal end, and the distal end of the inflation lumen is sealed closed.

The tube may be formed by extrusion from a suitable plastic such as nylon, polypropylene, or the like, although the present invention is not limited by the method of manufacture or the type of material, and injection molding or other materials could be used where feasible. The plastic material utilized in the manufacture of the tube should in any event, be sufficiently stiff so as to be capable of being advanced through an introducer cannula or sheath introducer, but not so stiff that it will cause damage to tissue.

The inflation lumen 28 extends fully between the proximal end and distal ends of the tube 22. As noted above, the inflation lumen is sealed at the distal end and carries a valve (not shown) at the other end, through which an inflation fluid, such as sterile water, may be injected. Such a valve is well known in medical product design and thus it will not be described in detail here. The diameter of the inflation lumen may vary, depending on the particular application. Typically, however, the diameter should be sufficiently large to permit ready inflation of the inflatable means.

In the embodiment of the wound treating device shown in FIGS. 3 and 4, an inflatable means 32 is located on the distal end 24 of the tube 22 for retention of the tube at the desired location and/or for applying a wound treating agent, although other types or forms of retention means may also be used for retaining the distal end of the clotting device at a selected position. In one form, the inflatable means 32 comprises a flexible sleeve located within a recessed area 44 at the distal end 24 of the tube 22. Each end of the sleeve is adhered or bonded to the surface of the tube, within the recessed area, to define an inflatable balloon portion therebetween. Any suitable solvent, adhesive, or the like may be used to adhere or bond the sleeve to the tube. Inflation aperture 29 extends through the wall of the tube, to provide a fluid flow path between the inflation lumen and the unadhered portion of the sleeve, to permit inflation of the balloon. The sleeve and recessed area preferably have the same length and the recessed area is preferably recessed an amount equal to the thickness of the sleeve, so that the exterior surface of the tube will be smooth and essentially uninterrupted after the sleeve is attached. The surface of the balloon and the distal end of the tube may be treated with any suitable release agent so as to prevent breaking of any clot that has formed when the inflation means is deflated and the device eventually withdrawn from the patient.

Although the inflation means may also be used to apply the wound treating agent, as described in more detail later, in this embodiment, to treat a wound and particularly to assist in forming a blood clot at the site of the vessel aperture, a quantity of treating or clotting agent 34 is preferably located in the second lumen 30, for ejection onto the vessel opening or wound. When the treating agent is a clotting agent, it may be any of the suitable clotting agents presently commercially available. For example, the clotting agent 34 may be a thrombin agent. A thrombin agent is frequently used as a topical treatment by vascular surgeons to stop surface bleeding after a large incision is made in the body. By dispensing thrombin agent onto an aperture in an artery, bleeding from the aperture can be reliably hastened and stopped, reducing the risk of a hematoma, and eliminating the need for an overnight stay in the hospital. The treating agent, which is preferably in foam, powder, or gel form, may be pre-filled into the second lumen during manufacture or may be inserted into the second lumen at the time of the procedure.

The treating agent is deposited at the site of the aperture or wound from the distal end of the tube 22. The means, generally at 36, for dispensing the treating agent 34 is preferably a plunger 38, as shown in FIGS. 3 and 4. The plunger 38 has a distal end, generally at 46, and a proximal end, generally at 48. A rod 50 extends between the distal and proximal ends of the plunger. A piston or grommet 52 is located at the distal end of the rod 50 and a thumb rest 54 is provided on the proximal end. By advancing the plunger 38, the piston 52 forces the agent 34 from the distal end 24 of the tube 22. Calibrations may be provided on the rod and/or tube to provide an indication of the amount of agent dispensed and the rate of dispensing. In FIG. 3, the piston 52 of the plunger 38 is nearer the proximal end 26 of the tube 22 and has not yet been advanced towards the distal end 24 of the tube 22. FIG. 4 illustrates the piston 52 being advanced towards the distal end 24 of the tube 22, ejecting the agent 34. FIG. 4 also depicts inflation of the inflatable means 32 by injection of a fluid 40 (which may be gas or liquid, but is preferably liquid such as sterile water) into the inflation lumen 28 to retain the distal end 24 at some selected location in the patient.

Figure 5:
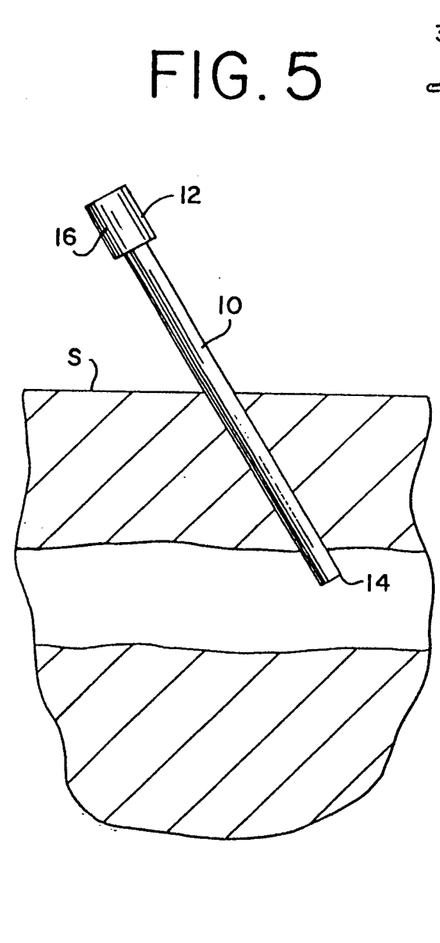
FIG. 5 is a side view of a sheath introducer which has been introduced through the skin and into a blood vessel.
Figures 6, 7:
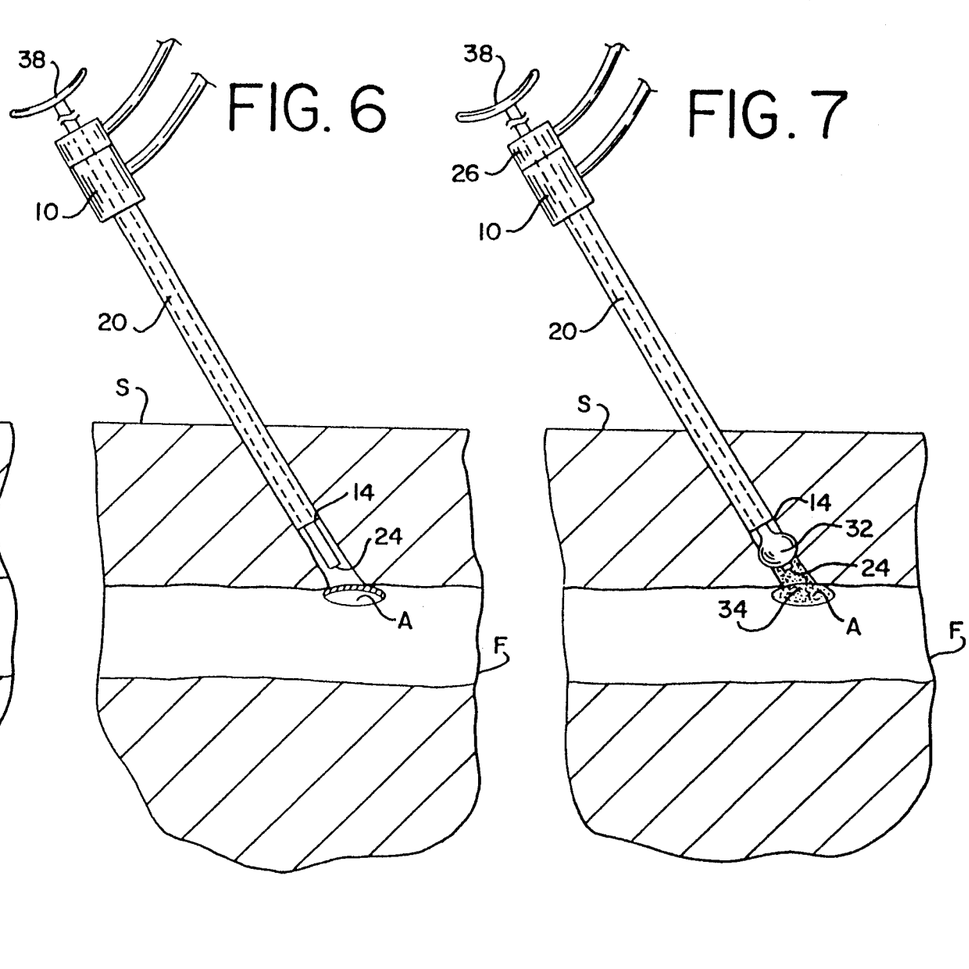
FIG. 6 is a side view depicting one of the steps of the method of the present invention, utilizing the wound treating or clotting device depicted in FIGS. 2, 3, and 4, where the sheath introducer of FIG. 5 has been retracted from the blood vessel and the wound clotting device has been inserted into the introducer.
FIG. 7 is a side view depicting another of the steps of the method of the present invention where the treating or clotting device of FIGS. 2, 3, and 4 is utilized to dispense clotting agent onto an aperture in a blood vessel.

Use of this embodiment of the present invention in forming a vascular clot is depicted diagrammatically in FIGS. 5-7. FIG. 5 shows an introducer cannula, for example the sheath introducer 10, which previously has been inserted through the skin surface into a femoral artery F, and following removal of the particular medical device.

As shown in FIG. 6, the introducer 10 is retracted out of the artery F, leaving an aperture or opening A in the wall of the artery F. The introducer 10 is retracted until it is out of the artery and spaced from the artery (although it is not completely removed, and remains in the proximity of the artery). The wound clotting device 20, as described above, is then inserted through the valve 12 of the introducer 10 and into the introducer 10. The device 20 is then advanced through the introducer 10 until the distal end 24 of the clotting device 20 extends beyond the distal end 14 of the introducer 10 and is adjacent to the aperture A in the artery F. To assure that the device is advanced the proper amount, the device may be of a selected length for each particular brand of introducer sheath used, or have indicia along the length of the tube 22 to indicate how far it should be advanced for each particular brand or style of introducer sheath.

As shown in FIG. 7, the inflatable means 32 is then inflated to retain or hold the distal end 24 of the clotting device 20 adjacent to the artery F. Accordingly, the distal end 24 cannot be pushed into the aperture A or pulled away from the aperture A. The plunger 38 is then advanced and the clotting agent 34 is dispensed from the distal end 24 of the tube 22 and onto the aperture A of the artery F. The clotting agent 34 will greatly hasten clotting and assist in preventing further bleeding from the aperture A.

The inflatable means 32, on the distal end 24 of the clotting device 20, may also be manually pressed and held against the aperture A in the artery F to assist clotting. This step is done after the inflatable retention means 32 has been inflated and the clotting agent has been dispensed onto the aperture A. By pressing the inflatable retention means 32 against the artery F, pressure is put on the aperture A to assist the clotting agent 34 in clotting the bleeding from the aperture A. Finally, after sufficient time for clotting has elapsed, the retention means 32 is deflated and the clotting device 20 and the introducer 10 are withdrawn from the patient's body, leaving no substantial amount of foreign material within the patient's vascular system.

An alternate embodiment of the wound treating device of the present invention is shown in FIGS. 8–15. The device of FIG. 8 includes an elongated tube 56, preferably extruded of suitable plastic material, which extends between a proximal end portion 58 and a distal end portion 60. The tube also includes a hollow bore or lumen 62, which extends fully between the proximal and distal end portions.

Figure 8:
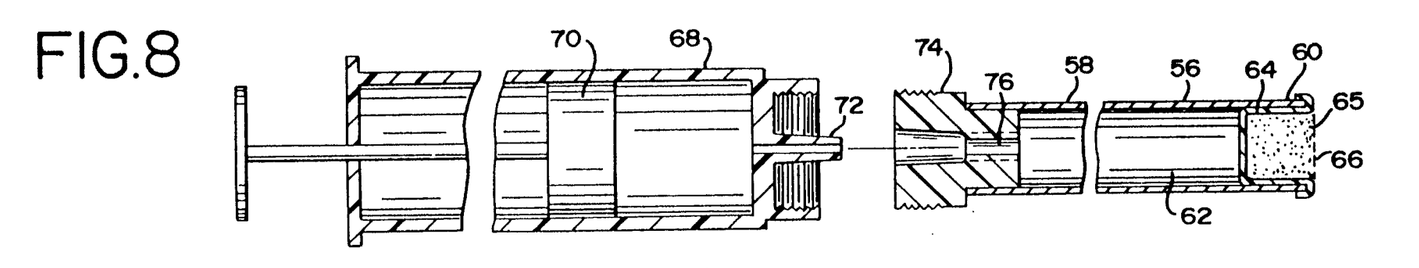
FIG. 8 is an enlarged cross-sectional view of the proximal and distal end portions of an alternate wound treating device, having an expandable retention and dispensing means in the form of a balloon membrane at the distal end.

For dispensing a treating agent at the site of a wound and for retaining the device in the vicinity of the wound, a flexible membrane 64 is attached at the distal end 60 of the tube 56. The membrane preferably has the shape of a short balloon, open at one end for attachment to the tube and closed at the other end. Other shapes, however, may also be used without departing from the present invention.

The membrane is preferably made of a flexible plastic material of the type which is compatible with medical applications, such as silicone, polyethylene, polypropylene, polyurethane, latex or the like. Prior to use, the balloon is located in an inverted or invaginated position within the distal end of lumen 62. When in this position, the membrane forms a pocket, into which treating agent 65 may be placed. The treating agent 65 may be of any desired material, such as an antibiotic, thrombin or clotting agent, in powder, gel or other suitable form. The treating agent may be pre-inserted into the tube during the manufacturing process or may be added to the tube at the time of use. If pre-inserted during manufacture, a removable hermetic seal 66 may be provided by adhesive bond or other suitable attachment over the distal end of the tube to preserve the treating agent against degradation during storage. The seal may be removed prior to use, or may be made of a material which dissolves upon contact with liquid such as bodily fluids or blood encountered when inserting the device into position adjacent the wound site.

Figure 9:
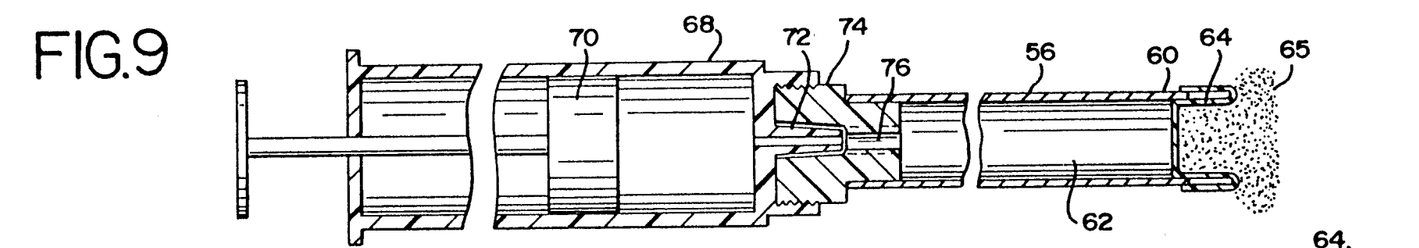
FIG. 9 is an enlarged cross-sectional view showing the wound treating device of FIG. 8 in an advanced stage of dispensing a treating agent.
Figure 10:
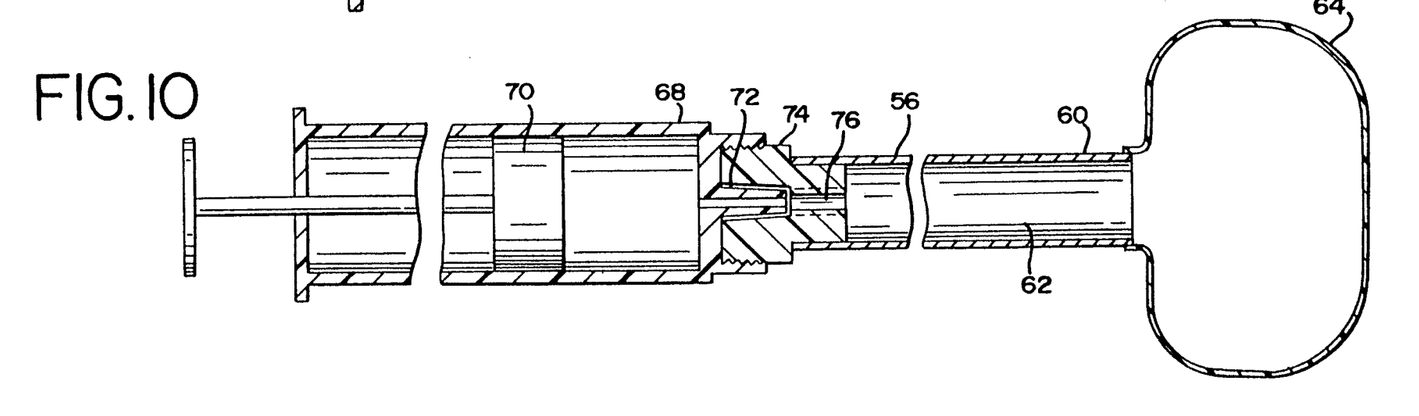
FIG. 10 is an enlarged cross-sectional view showing the embodiment of FIG. 8 after all the treating agent has been dispensed and the membrane inflated.
Figure 10A:
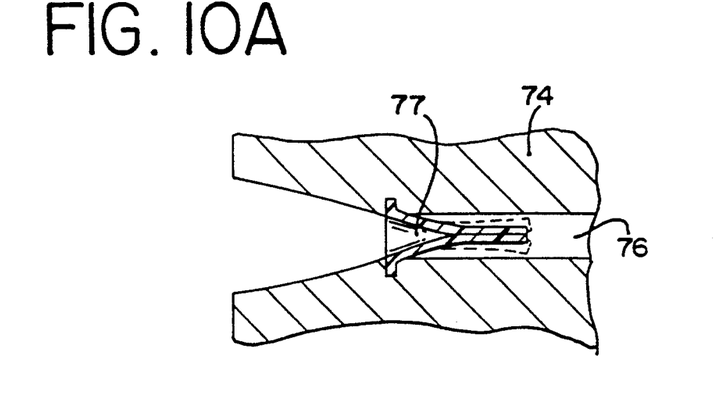
FIG. 10A is an enlarged cross-sectional view of a one-way valve that may be used to maintain inflation of the membrane.
Figure 11:
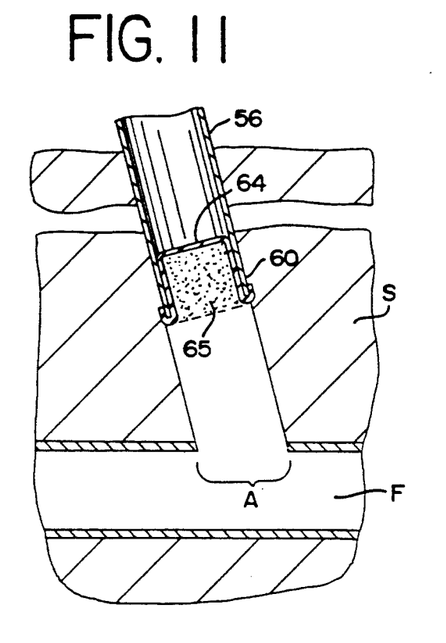
FIG. 11 is a cross-sectional view of the distal end of the treating device in FIG. 8 inserted into the skin, approaching a blood vessel.

To dispense the treating agent, as shown in FIGS. 9 and 10, the lumen 62 is pressurized by liquid or gas to push or inflate the membrane, causing it to expel the treating agent from the distal end of the lumen. Preferably a syringe of typical construction having a barrel 68, plunger or piston 70 and male luer fitting 72, is used to pressurize the lumen. To accommodate such a syringe, a female luer connector fitting 74 is provided at the proximal end of the tube 56. The fitting 74 includes a through passageway 76 which directly communicates at one end with the lumen and communicates at the other end with a standard tapered female luer connector. Although a luer-slip or luer-lock connection may be used, the illustrated fitting 74 has external threads for threaded engagement with the syringe (to provide a luer-lock arrangement) which prevents inadvertent separation of the syringe and tube.

FIGS. 11–15 illustrate how the alternative device shown in FIGS. 8–10 may be used in treating a wound and, in particular, in assisting clotting of an opening in a blood vessel F. As shown in FIGS. 11–14, the device may be used without an introducer sheath, although an introducer sheath is normally preferred. The distal end of the tube is inserted through the skin S to the site of the opening or aperture A in the blood vessel F. As noted above, the tube 56 may be inserted through an introducer or it may be introduced through an opening in the skin provided by another instrument. The tube is inserted until the distal end is generally adjacent to the wound.

Figure 12:
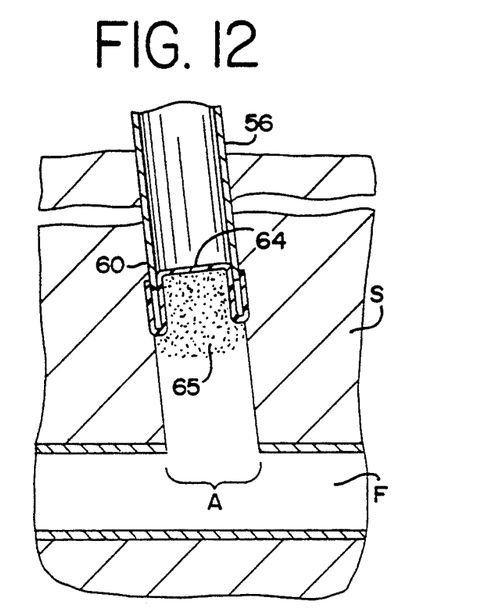
FIG. 12 is a cross-sectional view of the treating device of FIG. 8 showing clotting agent being dispensed at the aperture of a blood vessel.
Figure 13:
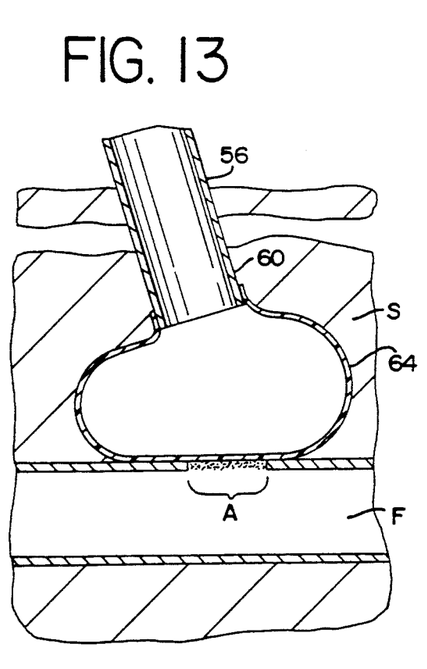
FIG. 13 is a cross-sectional view of the treating device of FIG. 8 showing the membrane fully inflated after the clotting agent has been dispensed, and being held against the wound.

The lumen of the tube is then pressurized, such as by high pressure liquid or air preferably liquid, injected into the lumen from a syringe. The pressure forces the membrane outwardly, expelling the treating agent at the site of the wound, as shown in FIG. 12. Continued application of pressure causes the membrane to expand to completely expel the treating agent 65 and form a balloon-like projection, as shown in FIG. 13, which has several advantages. First, when fully inflated, the balloon-like projection serves to retain the tube in the desired position relative to the site of the wound. When used to assist clotting in blood vessels, the balloon-like projection further helps block blood flow from the vessel and applies pressure against the vessel opening. The pressure applied by the balloon may also be supplemented manually by user force exerted on the proximal end of tube 56.

To avoid the need to maintain pressure on the syringe, the wound clotting device may include a releasable one-way inflation valve positioned, for example, in the inflation lumen which would allow syringe to be removed and the balloon to remain inflated in a position against the hole in the artery to block blood flow without a medical attendant being present. Such a valve could be of any suitable known type, such as a flexible duckbill or diaphragm valve 77 located in the passageway 76 of luer fitting 74 as is illustrated, for example, in FIG. 10a—depicted in the closed position in solid lines and in the open position in dashed lines.

Figure 14:
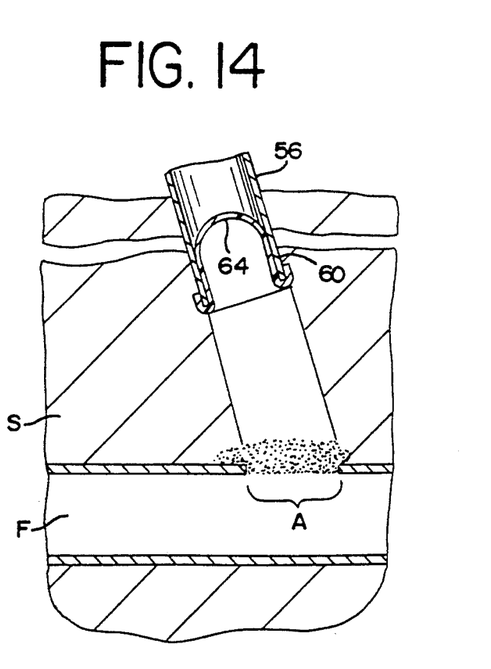
FIG. 14 is a cross-sectional view of the wound clotting device of FIG. 8 showing the wound clotting device being removed from the aperture after deflation of the membrane.

After the treatment is completed, the balloon is deflated and the tube 56 withdrawn, as shown in FIG. 14. To allow release of the membrane from the wound, the membrane is preferably coated with a non-stick release agent which will be described in more detail in reference to FIGS. 16–18.

Figure 15:
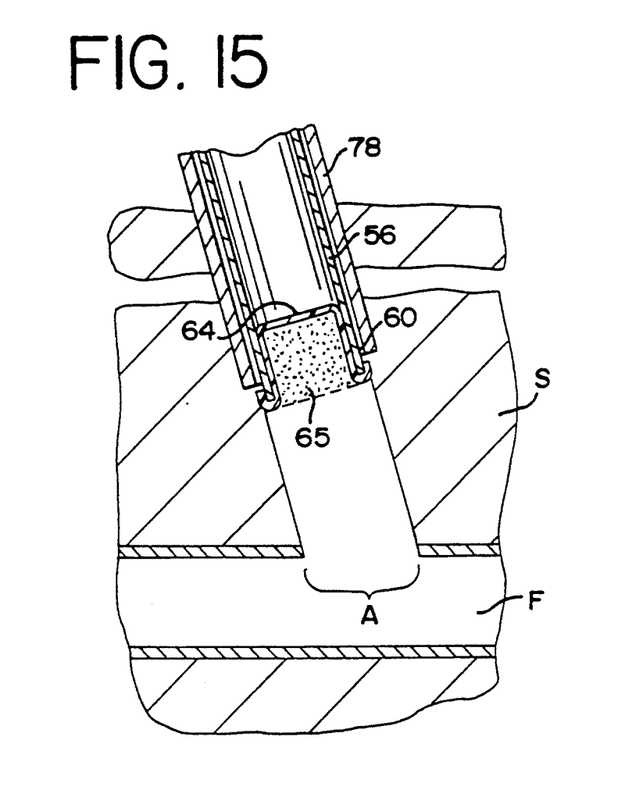
FIG. 15 is a cross-sectional view of the wound clotting device of FIG. 8 used in conjunction with a sheath introducer.

FIG. 15 depicts use of the alternate device in combination with an introducer sheath 78. When used with an introducer sheath, the tube 56 should be of sufficient length to extend beyond the distal end of the sheath to permit ejection of the treating agent at the wound site and to permit inflation of the membrane to form the balloon-like projection. Otherwise, the construction and operation of the alternate device with an introducer sheath is essentially as described above. Of course, when used with an introducer sheath which extends into the wound itself, e.g., into an access opening in a blood vessel, the sheath is normally withdrawn from the wound before the tube 56 is moved through the distal end of the sheath to dispense the treating agent.

Figure 16A:
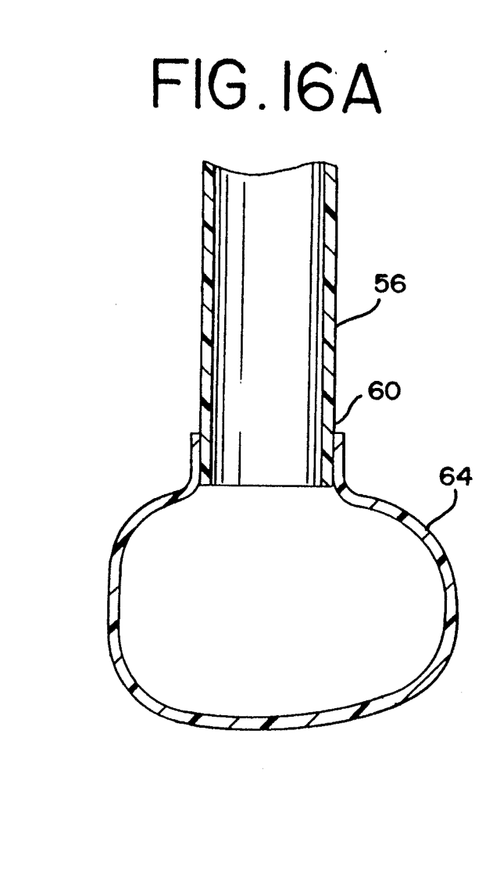
FIGS. 16A–C show steps in applying a release agent and a treating agent to the surface of the membrane.
Figure 16B:
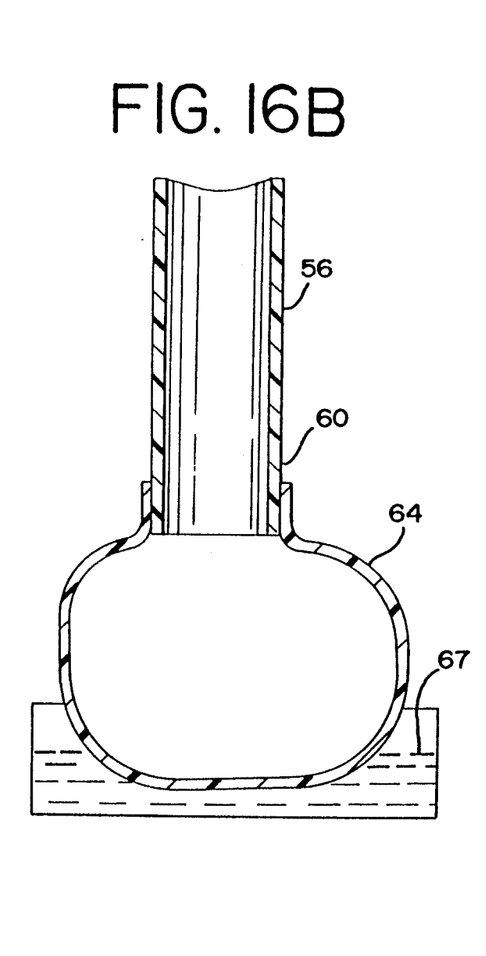
Figure 16C:
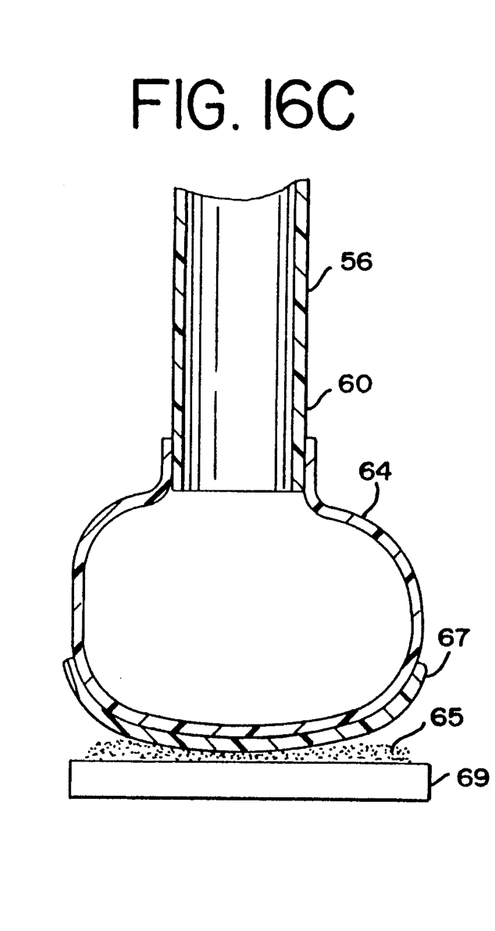
Figure 17:
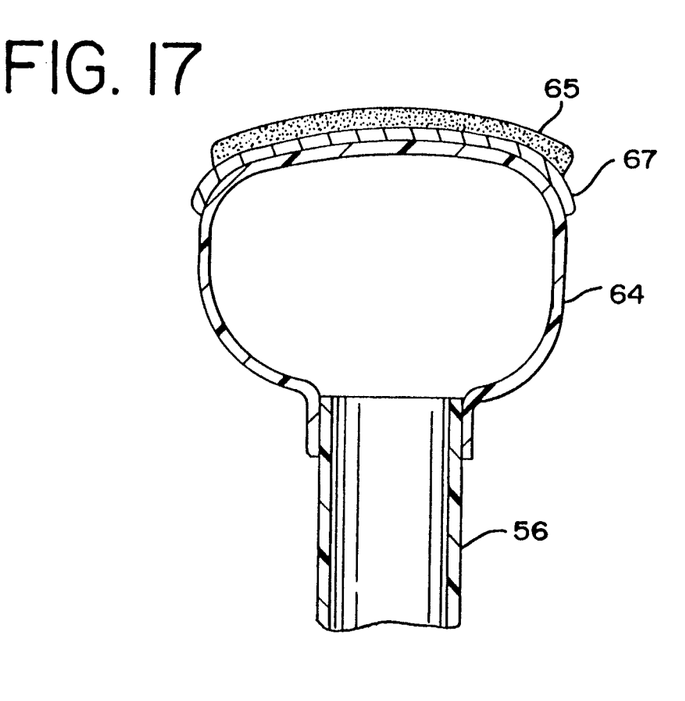
FIG. 17 is a cross-sectional view showing the inflated membrane in a balloon-like shape having a release agent and a treating agent applied.

FIGS. 16A–16C depict a method for applying the desired release agent and treating agent to the surface of the membrane 64. First, the membrane 64 is expanded to a balloon-like shape. The membrane is then dipped or inserted into a container containing a release agent 67, for example, a moisture activated release agent, such as a starch. The thickness of the release layer depends on the material chosen and the viscosity of the material at the time of application. The thickness is also dependent on the speed of hydration, which is a function of the mass of the release agent and the exposed surface area. It is presently believed that the preferred thickness of the release agent for a vascular wound, such as the incision in a blood vessel made for angiographic procedures, is approximately 10–50 mils.

Figure 18:
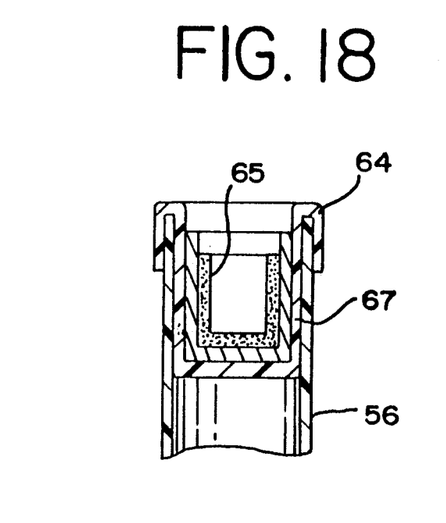
FIG. 18 is a cross-sectional view of the membrane, the release agent and the treating agent positioned within the tube.

The portion of the expanded membrane surface covered by the release agent is then placed in contact with a treating agent 65. A non-stick surface 69 such as Teflon material is preferably used to support the treating agent, and the inflated balloon is brought into contact with the treating agent so as to allow the agent to adhere to the membrane surface over the release agent. After the material on the membrane is dry as shown in enlarged dimension, for example, in FIG. 17, the membrane is drawn, as by suction, into an invaginated position within the tube as shown in FIG. 18.

Alternatively, the membrane 64 may itself be made of a material which has thrombogenic qualities, eliminating the need for a separate clotting agent. Specifically, the membrane could be made of a material having a specific activity which promotes clotting. It is understood that latex and some commercial grades of silicon rubber are naturally thrombogenic and promote clotting. Alternatively, other balloon materials, such as polyamide or PET, may be subjected to radiation or chemical treatment to increase surface activity to enhance clotting.

A further alternative embodiment of the present invention is depicted in FIGS. 19A-D. The embodiment of a wound treating device shown there has a detachable membrane, which may be left adjacent to the wound while the remainder of the device is removed. This embodiment comprises a plastic tubular portion 56 having a distal end 57, a proximal end 58 and a lumen 62 extending therebetween. A fitment 82 is carried at the proximal end of the tubular portion 56 and an inflation cannula 84 extends from the fitment, through the tubular portion to approximately the distal end 57 thereof.

More particularly, the fitment 82 is preferably of rigid molded plastic construction with a hollow distal end portion 86 sized for slidably receiving the proximal end 58 of the tubular portion 56 therein. A female luer taper bore 88 is provided at the proximal end of the fitment for receiving the standard male luer fitting of a syringe or similar pressurization means 90. Cannula 84 is coaxially and fixedly mounted within the fitment in communication with the female luer bore, and extends through the hollow distal end of the fitting and through the tubular portion 56.

The proximal end of the tubular portion 56 is attached to the fitment in a manner which permits at least limited axial movement of the tubular portion relative to the fitment and cannula. In the illustrated embodiment, the proximal end of the tubular portion has an enlarged, radially extending flange 92 slidably received within the open distal end of the fitment 86. Inturned end flange 94 of the fitment retains the proximal end of the tubular portion within the fitment and prevents inadvertent withdrawal of the tubular portion from the collar. As assembled, the proximal end flange 92 of the tubular portion is slidable between the inturned end flange 94 and internal shoulder 96 in the open end of the fitment.

The proximal end of the fitment 82 is preferably threaded at 98 for making a lure-lock connection with the syringe 90 or such other means as is desired for inflating the membrane. Alternatively, the syringe may be pre-attached to the proximal end of fitment. In either situation, the syringe or the fitment may also include a pressure-limiting aperture 100 (shown, for example, in the syringe) which limits the pressure that may be applied to the inflation membrane.

In accordance with this embodiment of the present invention, the membrane 64 may be separated from the tubular portion 56 after inflation at the wound site. This is achieved by providing a piercable, resealable portion 102 of the membrane removably positioned at a location within the distal end of tubular portion 56, and by defining a pressurization chamber 104 within the tubular portion proximal of the membrane. An inflation passageway such as in the form of the cannula 84 is provided in the tubular portion, and is of sufficient length to extend, if desired, through the pressurization chamber and through the piercable, resealable portion 102 of the membrane. When extending through the piercable portion of the membrane, the membrane may be expanded by passage of pressurized liquid or gas through the inflation passageway. After inflation, the cannula may be withdrawn into the pressurization chamber 104, which is defined in part by the partition or plug 106, where the pressurization by injection of liquid or gas discharges or expels the membrane from the distal end of the tubular portion so that the tubular portion may be withdrawn, leaving the inflated membrane at the wound site.

This may be achieved with the illustrated embodiment wherein the membrane is sealed to the piercable portion 102. Piercable portion 102 is positioned within the distal end of the tubular portion. The diameter of the piercable portion 102 is slightly larger than the inside diameter of the lumen so as to be frictionally retained therein but expellable with pressure. The piercable portion 102 may be of any suitable material biocompatible such as silicone or may be made of a material which eventually dissolves or decomposes upon contact with bodily fluids.

Figure 19A:
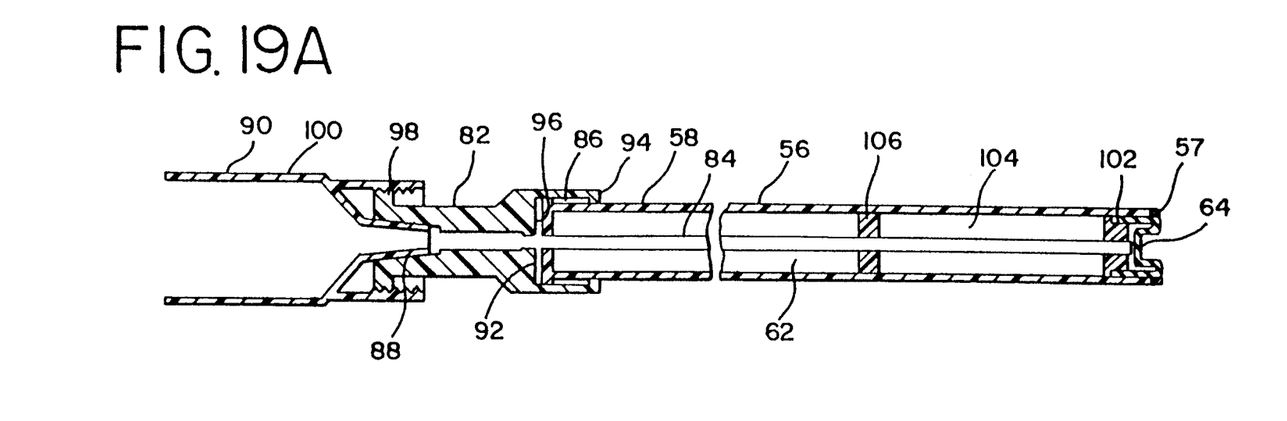
FIGS. 19A–D show an alternate embodiment of the wound treating device, in sequential operative positions, having a detachable membrane.

As shown in FIG. 19A, the piercable portion 102 is preferably located at sufficient distance from the distal tip end portion of the tube so that the membrane 64 may be positioned in the invaginated position with the distal end of the tube, leaving a space between the piercable portion 102 and the invaginated membrane to reduce the chance of inadvertent membrane puncture when the cannula 84 pierces the piercable portion.

Figure 19B:
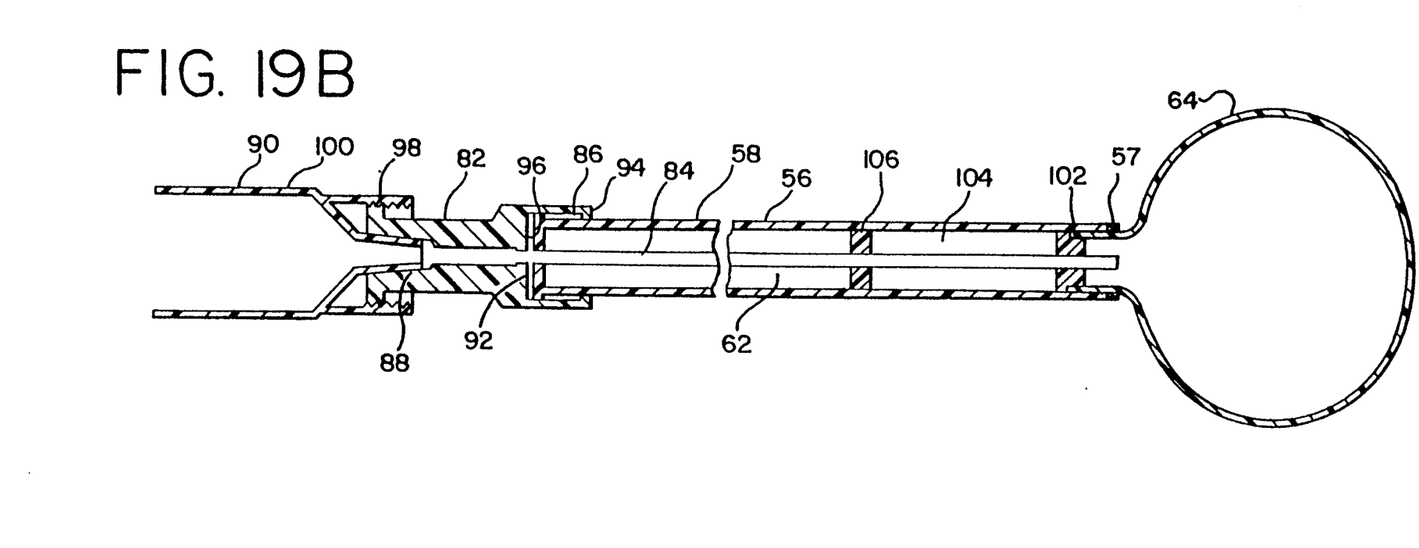

More particularly, the operation of the illustrated device with detachable membrane is most easily described in two steps. The first step includes expanding the membrane and the second step includes detaching the membrane, including piercable, resealable portion 102. To allow for expanding the membrane of the wound treating device, the tubular portion including flange 92 is positioned within the fitment in a first position, as shown in FIG. 19A, where flange 92 is positioned adjacent shoulder 96 of the fitment. When in the first position, the cannula 84 extends through the piercable portion of the membrane such that the end of the cannula is positioned within the interior of the membrane. As pressure is applied by way of the syringe, the membrane is expanded to a balloon-like shape outside the tubular portion, as shown in FIG. 19B, simultaneously applying any associated treating agent to the wound and applying pressure to the wound in the same manner as described in the prior embodiment.

Figure 19C:
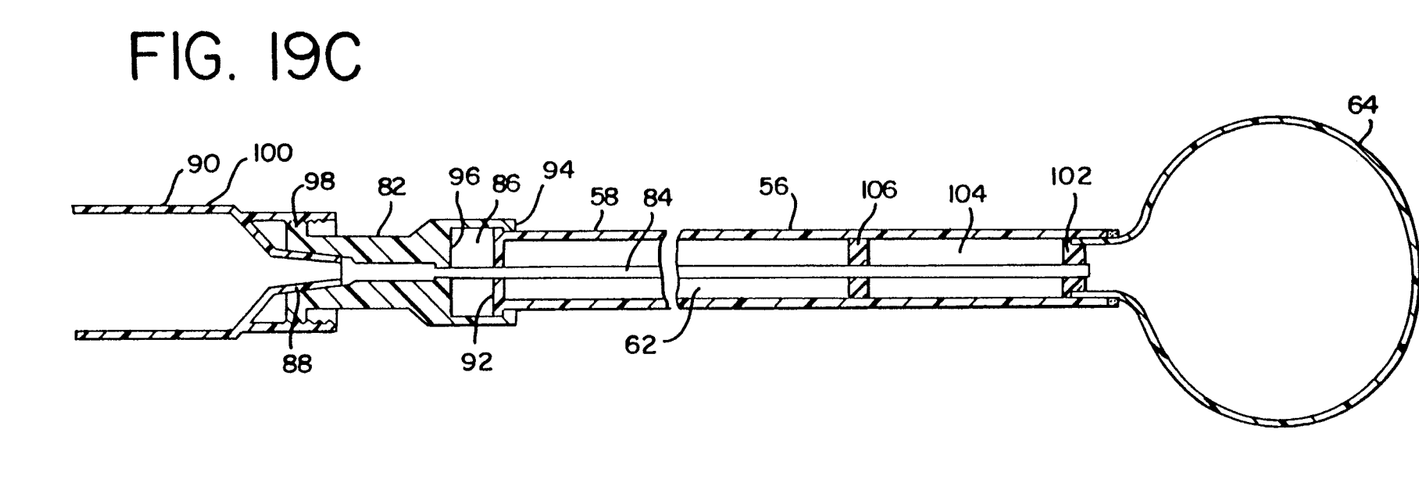

In order to detach the membrane from the device, the tubular portion is moved axially relative to the syringe and fitment to a second position as shown in FIG. 19C such that the flange 92 of the tubular portion is near or abuts the inturned flange 94 of the hollow distal end portion of the fitment. In the preferred embodiment, the fitment is shaped (for example, with an internal detent) such that when the tubular portion is moved to the second position, flange 92 slides into the fitment detent. Preferably, the movement of the tubular portion is accomplished by manually retracting the syringe and fitment slightly while holding the tube fixed. Although the axial movement of the tube is accomplished in this embodiment by sliding the tube relative to the fitment, relative axial movement could also be achieved by rotation if the fitment and tube were threadedly instead of slidably attached.

When the tubular portion is in the second position, the end of the cannula is positioned within the chamber 104 defined within the tube between partition or plug 106 and piercable, resealable portion 102.

Figure 19D:
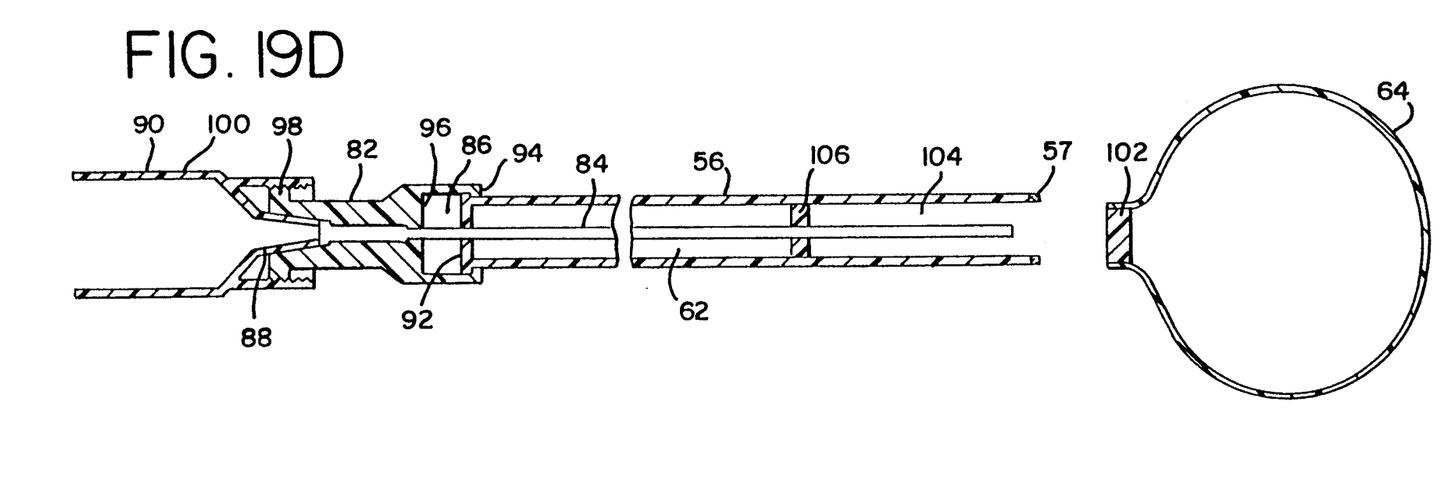

The pressurization chamber 104 is designed to allow the membrane 64 including piercable portion 102 to be expelled when the chamber is pressurized. Specifically, partition or plug 106 is securely attached to the tube. When pressure is applied to chamber 104 by way of the syringe, the membrane including the piercable portion 102 is forced out or expelled, as shown in FIG. 19D. This allows the tubular portion to be withdrawn, leaving the inflated membrane in the treating position at the wound site and permits any attending medical personnel to resume other duties. If constructed from biodegradable material, no subsequent deflation or removal is even required Although the preferred construction of the alternate device is described above, various changes may be made without departing from the present invention. The features of the wound treating device and method of the present invention have been described in connection with the accompanying drawings for purposes of illustration and not limitation. It is intended that this application include those modifications, variations and additions that would be readily apparent to one of ordinary skill upon reading this description. Accordingly, for ascertaining the scope of the present invention, reference must be made to the appended claims.

We claim:

1. A wound treating device comprising:
   a tubular portion having a proximal end, a distal end and a lumen extending therebetween;
   inflatable means cooperatively associated with said distal end of said tubular portion, said inflatable means comprising a flexible membrane carried at said distal end of said tubular portion and being positionable within said distal end and movable between a retracted position and an inflated position to form a balloon-like projection at said distal end when moved to the inflated position;
   said proximal end of said tubular portion being adapted to receive means for moving said inflatable means between said retracted position and said inflated position; and
   a wound treating agent disposed within said distal end of said tubular portion when said inflatable means is in said retracted position and said wound treating agent being discharged from said distal end by said inflatable means when said inflatable means is moved to said inflated position.

2. The wound treating device of claim 1, wherein said membrane is positionable within said distal end to form a pocket for receiving said treating agent.

3. The wound treating device of claim 1, wherein a release agent is disposed on said membrane.

4. The wound treating device of claim 1, wherein said balloon-like projection extends from said distal end and wherein said projection is adapted to permit the application of pressure directly on the wound site when in the inflated position.

5. The wound treating device of claim 1, wherein said membrane closes the distal end of said lumen, whereby pressurization of said lumen moves said membrane from the retracted position to the inflated position.

6. The wound treating device of claim 1, wherein said wound treating agent is disposed on the surface of said membrane.

7. The wound treating device of claim 1, further comprising a second lumen extending from said proximal end of the tubular portion to said distal end of said tubular portion for inflating said inflatable means.

8. The wound treating device of claim 1, further including a sheath introducer extending between said proximal end and said distal end for guiding said tubular portion toward the wound.

9. A wound treating device comprising:
   a tubular portion having a proximal end, a distal end and a lumen extending therebetween;
   inflatable means cooperatively associated with said distal end of said tubular portion, said inflatable means comprising a flexible membrane carried at said distal end of said tubular portion and being positionable within said distal end and movable between a retracted position and an inflated position to form a balloon-like projection at said distal end when moved to the inflated position;
   said proximal end of said tubular portion being adapted to receive means for moving said inflatable means between said retracted position and said inflated position; and
   wherein said membrane has a clot-promoting surface.

10. A method for treating wounds comprising the steps of:
    providing a wound treating device comprising:
      a tubular portion having a proximal end, a distal end and a lumen extending therebetween;
      inflatable means cooperatively associated with said distal end of said tubular portion, said inflatable means comprising a flexible membrane carried at said distal end of said tubular portion and being positionable within said distal end and movable between a retracted position and an inflated position to form a balloon-like projection at said distal end when moved to the inflated position;
      said proximal end of said tubular portion being adapted to receive means for moving said inflatable means between said retracted position and said inflated position; and
      a wound treating agent disposed within said distal end of said tubular portion when said inflatable means is in said retracted position and said wound treating agent being discharged from said distal end by said inflatable means when said inflatable means is moved to said inflated position;
    positioning said wound treating device in a location wherein said distal end is near the wound;
    moving said inflatable means to the inflated position to bring said wound treating agent into close association with the side of the wound;
    removing said treating device.

11. The method for treating wounds of claim 10 wherein said membrane is positionable within said distal end to form a pocket for receiving said treating agent.

12. The method for treating wounds of claim 10, wherein the wound treating device further comprises a release agent disposed on said membrane.

13. The method for treating wounds of claim 10 wherein said balloon-like projection is adapted to retain said tubular portion in the position near the wound.

14. The method for treating wounds of claim 10 wherein said balloon-like projection is adapted to provide pressure directly on the wound site during said step of moving said dispensing means to said inflated position.

15. The method for treating wounds of claim 10 wherein said membrane closes the distal end of said lumen, whereby pressurization of said lumen moves said membrane from the retracted position to the inflated position.

16. The method for treating wounds of claim 10 wherein said wound treating agent is disposed on the surface of said membrane.

17. The method for treating wounds of claim 10 further including providing a sheath introducer and inserting said tubular portion in said sheath introducer to guide said tubular portion toward the wound.

18. A method for treating wounds comprising the steps of:
   providing a wound treating device comprising:
      a tubular portion having a proximal end, a distal end and a lumen extending therebetween;
      inflatable means cooperatively associated with said distal end of said tubular portion, said inflatable means comprising a flexible membrane carried at said distal end of said tubular portion and being positionable within said distal end and movable between a retracted position and an inflated position to form a balloon-like projection at said distal end when moved to the inflated position;
      said proximal end of said tubular portion being adapted to receive means for moving said inflatable means between said retracted position and said inflated position; and
      said membrane having a clot-promoting surface;
   positioning said wound treating device in a location wherein said distal end is near the wound;
   moving said inflatable means to the inflated position to bring said clot promoting surface into close association with the site of the wound;
   removing said treating device.

19. A wound treating device comprising:
   a tubular portion having a proximal end, a distal end and a lumen extending therebetween;
   a fitment for receiving the proximal end of said tubular portion;
   said tubular portion and said fitment being relatively movable axially;
   means defining an inflation passageway attached to said fitment and extending through said tubular portion to approximately the distal end of said tubular portion;
   an inflatable means releasably carried by the distal end of said tubular portion, said inflatable means comprising a flexible membrane having a piercable resealable portion, said flexible membrane being movable between a retracted position and an inflated position; and
   means forming a pressurization chamber within said tubular portion adjacent said piercable portion of said inflatable means.
   whereby said means defining the inflation passageway may be moved between a position extending through said piercable resealable portion to inflate said membrane and a position terminating within said pressurization chamber to expel said membrane from the distal end of said tubular portion.

* * * * *